(12) United States Patent
Tschulena et al.

(10) Patent No.: US 10,172,994 B2
(45) Date of Patent: Jan. 8, 2019

(54) HEMODIAFILTRATION METHOD

(71) Applicant: Fresenius Medical Care Deutschland GmbH, Bad Homburg (DE)

(72) Inventors: Ulrich Tschulena, Frankfurt am Main (DE); Joachim Jankowski, Stahnsdorf (DE); Anselm Fabig, Zeuthen (DE); Carsten Mueller, Euerbach (DE)

(73) Assignee: FRESENIUS MEDICAL CARE DEUTSCHLAND GMBH, Bad Homburg (DE)

( * ) Notice: Subject to any disclaimer, the term of this patent is extended or adjusted under 35 U.S.C. 154(b) by 77 days.

(21) Appl. No.: 14/654,711

(22) PCT Filed: Dec. 19, 2013

(86) PCT No.: PCT/EP2013/003870
§ 371 (c)(1),
(2) Date: Jun. 22, 2015

(87) PCT Pub. No.: WO2014/095073
PCT Pub. Date: Jun. 26, 2014

(65) Prior Publication Data
US 2015/0343134 A1    Dec. 3, 2015

Related U.S. Application Data

(60) Provisional application No. 61/740,026, filed on Dec. 20, 2012.

(30) Foreign Application Priority Data

Dec. 20, 2012 (DE) .................. 10 2012 025 052

(51) Int. Cl.
*A61M 1/36* (2006.01)
*A61M 1/34* (2006.01)
*A61M 1/16* (2006.01)

(52) U.S. Cl.
CPC ............ *A61M 1/3639* (2013.01); *A61M 1/16* (2013.01); *A61M 1/3403* (2014.02);
(Continued)

(58) Field of Classification Search
CPC .... A61M 1/16; A61M 1/3403; A61M 1/3434; A61M 1/361; A61M 1/3612;
(Continued)

(56) References Cited

U.S. PATENT DOCUMENTS 6,193,681 B1    2/2001   Davidner et al.
7,066,900 B2 *  6/2006   Botto .................... A61M 1/16
                                                      204/450
(Continued)

FOREIGN PATENT DOCUMENTS

CN    1065798    11/1992
CN    2438454    7/2001
(Continued)

OTHER PUBLICATIONS

Vanholder et al. Review of uremic toxins: Classification, concentration, and interindivicual variablity, Kidney International, vol. 63 (2003), pp. 1934-1943.
(Continued)

*Primary Examiner* — Dirk R Bass
(74) *Attorney, Agent, or Firm* — Jacobson Holman, PLLC.

(57) ABSTRACT

The invention relates to a device for hemodiafiltration with an extracorporeal circulation (10) for receiving blood to be purified and having a hemodialyzer and/or hemofilter (20) which is connected to the blood circulation (10), such that the blood circulation (10) has at least one inlet line (12, 14) for the supply of a replacement fluid upstream and downstream from the hemodialyzer and/or hemofilter (20), characterized in that the apparatus also comprises measurement
(Continued)

Figure 1:
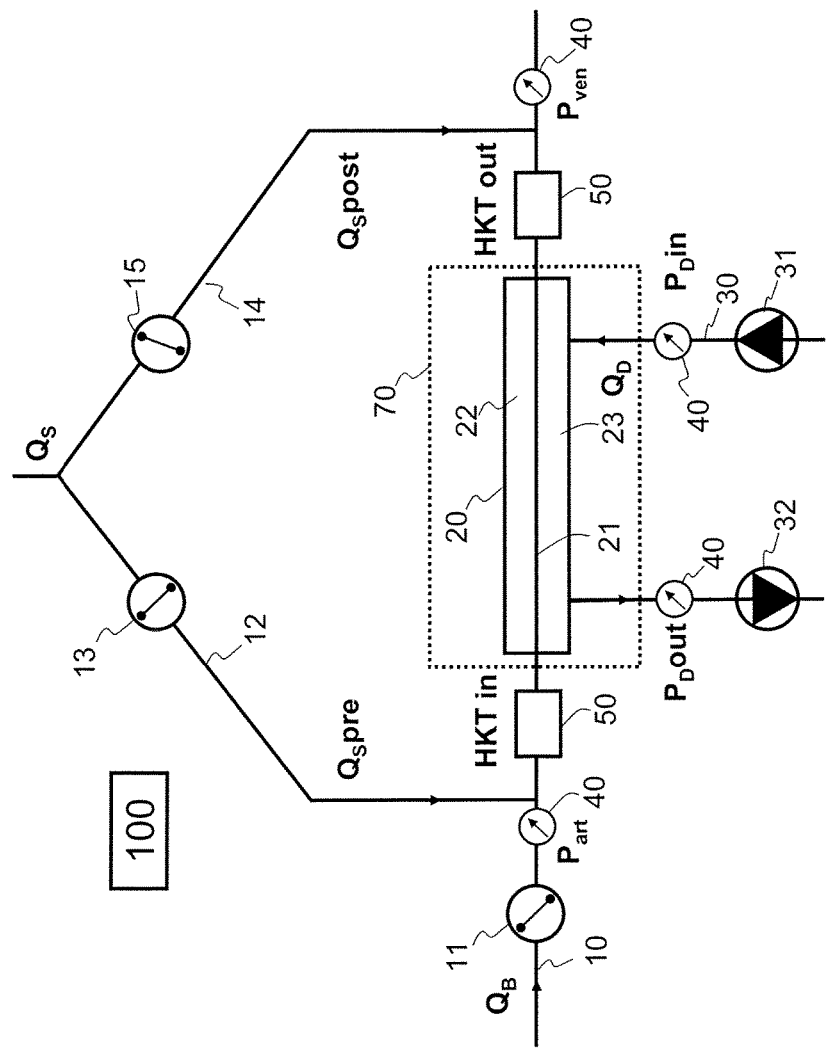

apparatuses for recording the transmembrane pressure and/or hematocrit (HKT) and/or blood density, such that the measurement apparatuses are connected to a control unit (100) for controlling one or more of the transmembrane pressure and/or the hematocrit (HKT) and/or the blood density, the control unit (100) being constructed so that the control is implemented with the help of at least one of the infusion rates ($Q_s$pre, $Q_s$post) of the replacement fluid (13, 15), and the blood to be purified is exposed to a high-frequency electromagnetic field and/or an electric DC field (70) before and/or during contact with the hemodialyzer and/or hemofilter (20).

9 Claims, 7 Drawing Sheets

(52) U.S. Cl.
CPC .......... *A61M 1/3434* (2014.02); *A61M 1/361* (2014.02); *A61M 1/3609* (2014.02); *A61M 1/3612* (2014.02); *A61M 1/3681* (2013.01); *A61M 2202/0445* (2013.01); *A61M 2202/0498* (2013.01); *A61M 2205/054* (2013.01); *A61M 2205/3344* (2013.01); *A61M 2230/207* (2013.01)

(58) Field of Classification Search
CPC .............. A61M 1/3639; A61M 1/3681; A61M 2202/0445; A61M 2202/0498; A61M 2205/054
USPC ................................................ 210/96.2, 137
See application file for complete search history.

(56) References Cited

U.S. PATENT DOCUMENTS

| | | |
|---|---|---|
| 8,216,478 B2 | 7/2012 | Noack et al. |
| 8,784,353 B2 | 7/2014 | Maierhofer et al. |
| 2002/0023880 A1* | 2/2002 | Pedrini .................. A61M 1/16 210/646 |
| 2005/0015040 A1 | 1/2005 | Wuepper |
| 2005/0082225 A1 | 4/2005 | Kreymann |
| 2009/0043346 A1* | 2/2009 | Palti ...................... A61N 1/326 607/2 |
| 2009/0079578 A1* | 3/2009 | Dvorsky ............. A61M 1/3656 340/604 |
| 2009/0221948 A1 | 9/2009 | Szamosfalvi et al. |
| 2010/0264086 A1* | 10/2010 | Noack .................. A61M 1/342 210/647 |
| 2011/0021966 A1* | 1/2011 | Leonard ............. A61M 1/3681 604/6.01 |
| 2012/0273415 A1* | 11/2012 | Gerber ................. A61B 5/0031 210/636 |
| 2013/0134077 A1* | 5/2013 | Wieskotten ......... A61M 1/3626 210/85 |

FOREIGN PATENT DOCUMENTS

| | | |
|---|---|---|
| CN | 1551795 | 12/2004 |
| DE | 2731744 | 2/1979 |
| DE | 19651355 | 6/1998 |
| DE | 10324668 | 12/2004 |
| DE | 102007052571 | 5/2009 |
| DE | 102008050849 | 4/2010 |
| DE | 102009001901 | 9/2010 |
| DE | 102010028902 | 11/2011 |
| EP | 2087916 | 8/2009 |
| FR | 2087416 | 12/1971 |
| JP | S59-062058 | 4/1984 |
| JP | H03114468 | 5/1991 |
| JP | H06304454 | 11/1994 |
| JP | 2002126075 | 5/2002 |
| JP | 2005527247 | 9/2005 |
| JP | 2005535361 | 11/2005 |
| JP | 2007325679 | 12/2007 |
| RO | 122077 | 12/2008 |
| WO | WO 98/50091 | 11/1998 |
| WO | WO 00/09182 | 2/2000 |
| WO | WO 03/094998 | 11/2003 |

OTHER PUBLICATIONS

Polaschegg et al. Hemodialysis machines and monitors, Replacement of Renal Function by Dialysis, Drukker, Parsons, and Maher, Kluwer Academic Publishers, 4. Edition 1996, pp. 333-379. unctions by Dialysis.

* cited by examiner

HEMODIAFILTRATION METHOD

The present invention relates to an apparatus for performing a hemodiafiltration treatment under the influence of an alternating electromagnetic field and/or a direct electric field.

The purpose of healthy kidneys is to eliminate end products of the metabolism (substances that must be eliminated in urine) and toxins (uremic toxins) from the body by forming the urine. The kidneys remove a broad spectrum of substances of different molecular weights. A review of uremic toxins was published by R. Vanholder et al. (R. Vanholder et al. Kidney International, 63 (2003) 1934-1943). The uremic toxins are divided into three classes and the basis of their molecular weight. Toxins with a molecular weight of less than 500 Dalton form the low-molecular-weight group. The medium-sized molecules are in a middle range with a molecular weight between 500 D and 12,000 D. The medium-sized molecules include, for example, $\beta_2$-microglobulin (11,800 D). The third class of uremic toxins is formed by molecules having a molecular weight of more than 12,000 D.

In addition, they are differentiated according to the water solubility of the uremic toxins. Examples of uremic toxins having good water solubility and a low molecular weight include urea, creatinine, oxalates, guanidines and uric acid.

Examples of uremic toxins having a low water solubility include p-cresol, indoxyl sulfate, phenol, hippuric acid and homocysteine. These uremic toxins are mainly bound to proteins when they are present in the serum.

In a healthy subject, uremic toxins are eliminated with the urine via the kidneys. In chronic renal failure, however, the uremic toxins remain in the patient's blood and must be removed by hemodialysis or peritoneal dialysis.

Although it is readily possible to remove water-soluble toxins, for example, urea or creatinine, by hemodialysis, it is extremely difficult to remove hydrophobic uremic toxins that have a poor solubility by hemodialysis methods due to protein binding. It is generally assumed that there is a chemical equilibrium between the free dissolved toxin and the protein-bound toxin, said equilibrium being shifted far to the side of the protein-bound toxin. This means that most of these uremic toxins are bound to protein and only a small portion are dissolved in the blood plasma.

Since a large portion of the substances are low-molecular components, only a small portion of which are present in free form, they are dialyzable in principle.

In addition, it is assumed that albumin functions as a binding partner of the hydrophobic uremic toxins. Albumin is retained by dialysis membranes because of its molecular weight. Albumin is not removed by hemodialysis methods. Thus only the free dissolved portion of the uremic toxins can be removed from the patient's blood. The rate-determining step is the establishment of an equilibrium during dialysis. Although it may be expected that after removing the dissolved toxins from the blood, an equilibrium would be re-established between the free toxins and the protein-bound toxins and that a substantial portion of the toxins could be removed if the dialysis time is long enough, but this time is not available in a hemodialysis treatment. There is thus a demand for dialysis processes which also remove the protein-bound uremic toxins from the patient's blood.

The present invention relates to a device for hemodiafiltration with an extracorporeal circulation to hold blood to be purified and with a hemodialyzer and/or a hemofilter, which is connected to the blood circulation such that the blood circulation has at least one inlet line for supplying a replacement fluid upstream or downstream from the hemodialyzer and/or hemofilter. Furthermore, the apparatus has means for generating a high-frequency electromagnetic alternating field and/or a unit for generating an electric DC field, such that the blood to be purified is exposed to the high-frequency electromagnetic alternating field and/or to the electric DC field before and/or during its contact with the dialyzer. The present invention thus makes available a method that shifts the position of the equilibrium between free and protein-bound toxins and accelerates the establishment of the equilibrium during the dialysis treatment.

Those skilled in the art are familiar with methods of hemodialysis and hemofiltration. A summary of the most important hemodialysis methods and machines can be found in the publications "Replacement of Renal Function by Dialysis" (Drukker, Parsons and Maher; Kluwer Academic Publishers, 4th edition 1996; and "Hemodialysis Machines and Monitors" by H. D. Polaschegg and N. W. Levin), the disclosure content of which is herewith referenced. In hemodialysis, a patient's blood is sent through an arterial bloodline and into the blood chamber of a dialyzer. The blood is normally transported with the help of a peristaltic rotary pump arranged in the arterial bloodline. After passing through the pump, the blood is passed through the blood chamber of the dialyzer and finally returned to the patient through a venous drip chamber and a venous bloodline connected thereto. A venous pressure monitor is connected to the venous drip chamber as a protective system for direct determination of blood loss to the environment. If necessary, the two needles required for the arterial and venous cannulas may be replaced by a single needle in the so-called single-needle dialysis. In this type of dialysis, the extracorporeal circulation consists of a single-needle cannula with a connected Y-piece. From the dialyzer, the venous line leads back to the Y-piece. The arterial and venous lines are alternately sealed by clamps. One or more blood pumps are in operation to ensure the alternating flow to and from the Y-piece.

In hemodialysis, the dissolved substances are removed from the blood by diffusion through the dialyzer membrane. Although a low transmembrane pressure is applied for ultrafiltration of the excess water from a patient, this filtration plays hardly any role at all for the purification of blood to remove specific substances.

Dissolved substances are removed in hemofiltration by convection and not by diffusion. At the same time, the ultrafiltrate is replaced almost completely by a replacement fluid with a composition similar to that of the dialysate in dialysis. In this method, the similarity with the natural kidney and the effective removal of larger molecules are emphasized. However, the removal of low-molecular substances is reduced in comparison with hemodialysis because at most 45% of the blood can be ultrafiltered in the so-called postdilution hemofiltration. Hemofiltration today is used on only a small number of patients because of the high cost of the commercial replacement fluid and the high blood throughput required to perform the treatment in a suitable period of time.

Hemofiltration machines for maintenance therapy comprise the same extracorporeal pump and monitoring systems as hemodialysis machines. The dialysate circulation is replaced by a liquid balancing and heating system. In the so-called predilution mode, replacement fluid is added to the blood upstream from the dialyzer and the filtrate is created by the corresponding transmembrane pressure. To be clinically effective, a very large amount of replacement fluid is necessary. Because of the high cost of commercial replacement fluid, this method has not yet been successful. More common is the postdilution mode because it requires less replacement fluid. In this mode, replacement fluid is added to the blood downstream from a dialyzer. Good purification coefficients are achieved in the postdilution mode. Normally about 20 to 24 liters of replacement fluid are added during a 4-hour treatment. However, the efficacy of this method is limited due to a critical transmembrane pressure above which the blood is damaged.

Various systems have been proposed for fluid balancing. In the gravimetric balancing method, ultrafiltrate can be withdrawn through the ultrafiltrate pump into a bag or container, which stands or is hung on a balancing platform. Replacement fluid from a bag or container on the same platform is pumped by an additional pump to the venous drip chamber. A net fluid withdrawal is achieved either through an additional ultrafiltration pump or through a programming unit which controls the substitution pump so that it supplies less fluid than is removed through the filtration pump.

Hemodiafiltration, which is a combination of hernodialysis and hemofiltration, may be performed by combining the extracorporeal circulation of a hemofiltration machine with that of a hemodialysis machine. Hemodialysis machines having volumetrically controlled ultrafiltration may easily be adapted for hemodiafiltration which is less expensive. This is especially beneficial from the standpoint of cost if the replacement fluid is prepared from the dialysis fluid online.

Treatment parameters such as the dialysate content (sodium concentration), the ultrafiltration rate and the throughput of blood and dialysate are varied during dialysis to increase or maintain efficiency and/or to reduce the symptoms that occur during dialysis. The change follows either a kinetic model or more often a "clinical evaluation." Symptoms occurring during dialysis, in particular low blood pressure, are closely associated with the ultrafiltration. In dialysis machines having ultrafiltration pumps, which are independent of the dialysate pumps, a profiling effect occurs due to the change in the ultrafiltration rate.

In summary, it can be concluded that in hemodialysis the patient's blood is purified by the fact that the substances to be removed from the blood diffuse through the membrane because of a concentration gradient across the membrane of the dialyzer and these substances therefore reach the dialysis fluid. The driving force in hemofiltration is essentially a pressure difference across the membrane which causes convective transport of substances through the membrane and, in doing so, purifies the blood especially of higher molecular substances. In hemofiltration and in the combined method of hemodiafiltration, liquid that must be replaced except for a small differential amount for controlling the fluid exchange is removed from the patient's blood.

Predilution is preferably used for patients having a higher risk of blood coagulation. This risk is reduced by dilution of the blood before the blood treatment.

Low hematocrit concentrations lead to large quantities of free, i.e., unbound water accordingly, which makes possible a characteristic convective transport of substances through the membrane. Accordingly, the cleaning effect may be greater in the case of moderate and high-molecular substances in the predilution mode than in the postdilution mode.

In addition, the predilution of the blood to be purified results in the fact that more protein-bound uremic toxins can enter the plasma and be dialyzed. With the present invention, it is therefore advantageous if the ratio of the infusion rates ($Q_s$pre, $Q_s$post) of the replacement fluid is controlled, so that $Q_s$pre is always greater than or equal to $Q_s$post. The ratio of the infusion rates $Q_s$pre/$Q_s$post is preferably at least 1.2.

To combine the advantages of the pre- and postdilution modes, it has also been proposed that the two modes be used simultaneously with a fixed ratio of the throughput of pre- and postdilution replacement fluid (L. Pedrini and V. De Cristofaro, Abstract at the EDTNERA Congress, Madrid, 1999).

The publication WO 98/50091 relates to a method for controlling a blood purification apparatus, which includes at least one inlet line to the blood circulation for supplying the replacement fluid upstream and downstream from the filter. A control unit is provided for monitoring a blood pump, an ultrafiltrate pump and the replacement fluid pumps and for monitoring means for weighing the corresponding quantity of fluid. The control unit monitors the pumps at predetermined intervals to adjust the instantaneous flow rate of the bloodstream, the ultrafiltrate and the substitution products.

The publication WO 00/09182 relates to a fluid drive device, which is suitable for remove certain blood elements and/or blood constituents by diffusion through a semipermeable membrane. This device is equipped with a blood pump, a pump for supplying predilution replacement fluid, a pump for feeding postdilution replacement fluid and an ultrafiltration pump. Valves are arranged in such a way that the liquid is passed through a container which can be brought into a liquid connection with each of the pumps in order to control the functioning of the pumps and consequently the flow rates of the corresponding liquids.

Another disadvantage of the postdilution mode consists of the fact that a limitation membrane is created on the membrane of the hemodialyzer and/or hemofilter during the blood purification. The thickness of this membrane increases with an increase in the length of the treatment, which reduces the permeability of the membrane. Therefore the cleaning effect is worsened—at a constant transmembrane pressure. If a constant purification effect is to be achieved, an increasing transmembrane pressure would be necessary, but this may result in damage to the membrane.

U.S. Pat. No. 5,578,223 discloses an artificial kidney which operates in a postdilution mode and is suitable for use in a hemofiltration, hemodialysis and hemodiafiltration treatment. To maintain a desired bicarbonate concentration in a patient's blood, the device includes means for perfusion of a bicarbonate-containing liquid into the extracorporeal circulation after passing through the exchange means and dosing means for adjusting the bicarbonate concentration in a patient's blood at a desired level. An extraction pump which is connected to the outlet of the exchanger is controlled by a control unit to maintain a desired measure of weight loss during the duration of the treatment. The flow rate of the bicarbonate solution is controlled by the control unit as a function of the flow rate of the extract pump, the desire bicarbonate concentration in a patient's blood and the concentration of the bicarbonate solution before perfusion into the extracorporeal circulation.

The object of the present invention is to provide a device for purification of blood by means of hemodialysis and/or hemofiltration with which the advantages of the predilution mode and the postdilution mode may be combined and in which the purification effect of the hemodialyzer and/or of the hemofilter for protein-bound toxins is improved at the same time.

Against the background of an apparatus according to the preamble of Claim 1, this object is achieved by the fact that the apparatus also comprises measurement apparatuses for recording the transmembrane pressure and/or the hematocrit and/or the blood density, wherein the measurement apparatuses are connected to a control unit (100) for controlling one or more of the transmembrane pressure and/or the hematocrit and/or the blood density, wherein the control unit is constructed so that the control is performed with the help of at least one of the infusion rates of the replacement fluid, and the blood to be purified is exposed to a high-frequency electromagnetic field and/or to an electric DC field before and/or during the contact with the dialyzer.

The apparatus according to the invention as defined in the preamble of Claim 1 has additional means for generating a high-frequency electromagnetic field and/or an electric DC field. The invention is based on the finding that the adjustment of the equilibrium between protein-bound and free toxins can be accelerated with the help of a high-frequency electromagnetic field and/or an electric DC field. Those skilled in the art are familiar with such means. The apparatus according to the invention may have, for example, a high-frequency capacitor, a high-frequency coil and/or a high-frequency electrode for generating a high-frequency electromagnetic field. The high-frequency electromagnetic field has a frequency of 100 kHz to 2 GHz, preferably 1 MHz to 1 GHz.

In addition, the apparatus according to the invention may have means for generating an electric DC field. Those skilled in the art are familiar with such means. The apparatus according to the invention may be constructed, for example, of a plate capacitor having two, four or more plates. The electric DC field has a field strength up to 1500 V/m. In a preferred embodiment the electric DC field has a field strength of 10 V/m to 400 V/m, especially preferably 100 V/m to 250 V/m. A rotating or traveling DC field can be generated by means of low-frequency reversal of the polarity of the capacitor plates.

The means for generating a high-frequency electromagnetic field and/or an electric DC field may be embodied and arranged in and/or on the blood circulation, such that the blood to be purified can be exposed to the high-frequency electromagnetic field before, during or even both before and during contact of the blood to be purified with the dialyzer and/or with the semipermeable membrane of the dialyzer.

By adding substitution solutions to the extracorporeal circulation upstream and downstream from the hemodialyzer and/or hemofilter, the advantages of postdilution and predilution can be combined on the one hand, i.e., satisfactory purification results are achieved for low-molecular substances and for medium- and high-molecular substances. On the other hand according to the present invention, the infusion rates of one or both replacement fluids supplied upstream and downstream may be used to control the operating parameters and/or blood parameters.

For example, in the case of a high transmembrane pressure or a high hematocrit value of the blood, the infusion rate of the substitution solution added upstream from the dialyzer may thus be increased until reaching the desired levels to be controlled or until the values drop below given limit values. Accordingly, in the case of a low transmembrane pressure or a low hematocrit, the infusion rate of the replacement fluid added downstream from the dialyzer may be increased, which leads to an improvement in the diffusive transport of substances, i.e., to an improved purification effect for low-molecular substances due to the resulting greater concentration gradient across the membrane.

The infusion rate of the substitution solutions added upstream from the hemodialyzer and/or hemofilter is preferably increased in comparison with the infusion rate of the substitution solutions added downstream from the hemodialyzer and/or hemofilter with an increase in the transmembrane pressure and/or an increase in the blood density and/or an increase in the hematocrit level of the blood. The transmembrane pressure and/or hematocrit and/or blood density may be detected continuously.

It is especially advantageous if the infusion rates of the substitution solutions are selected so that an essentially stationary limitation membrane is formed on the side of the membrane of the hemodialyzer and/or of the hemofilter opposite the chamber through which the blood flows. This yields the advantage that the efficiency and the spectrum of the screen coefficients of the hemodialyzer and/or of the hemofilter remain constant during the period of the treatment.

In addition, predilution of the blood to be purified results in more protein-bound uremic toxins entering the plasma and being dialyzed—in particular due to the influence of the electric field. It is therefore advantageous with the present invention if the ratio of the infusion rates ($Q_s$pre, $Q_s$post) of the replacement fluid is controlled so that $Q_s$pre is always greater than or equal to $Q_s$post. The ratio of the infusion rates $Q_s$pre/$Q_s$post is preferably at least 1.2. The ratio of the infusion rates $Q_s$pre/$Q_s$post is especially preferably at least 1.5.

The ratio of the infusion rates of the substitution solutions $Q_s$pre/$Q_s$post in the bloodstream can be altered after the end of the treatment to dissolve the limitation membrane. In this way, most of the proteins forming the limitation membrane can be returned to the patient after the end of the blood treatment.

The measuring devices may comprise pressure sensors each of which is arranged in the extracorporeal circulation and/or in the dialysis fluid circulation upstream and/or downstream from the hemodialyzer and/or hemofilter.

In another embodiment of the present invention, the measuring devices comprise sensors in the extracorporeal circulation upstream and/or downstream from the hemodialyzer and/or hemofilter for detecting the hematocrit.

According to a preferred embodiment, agents for controlling the at least one infusion rate ($Q_s$pre, $Q_s$post) are pumps in the inlet lines.

In another embodiment, the means for controlling the at least one infusion rate ($Q_s$pre, $Q_s$post) are valves in the inlet lines.

Figure 2:
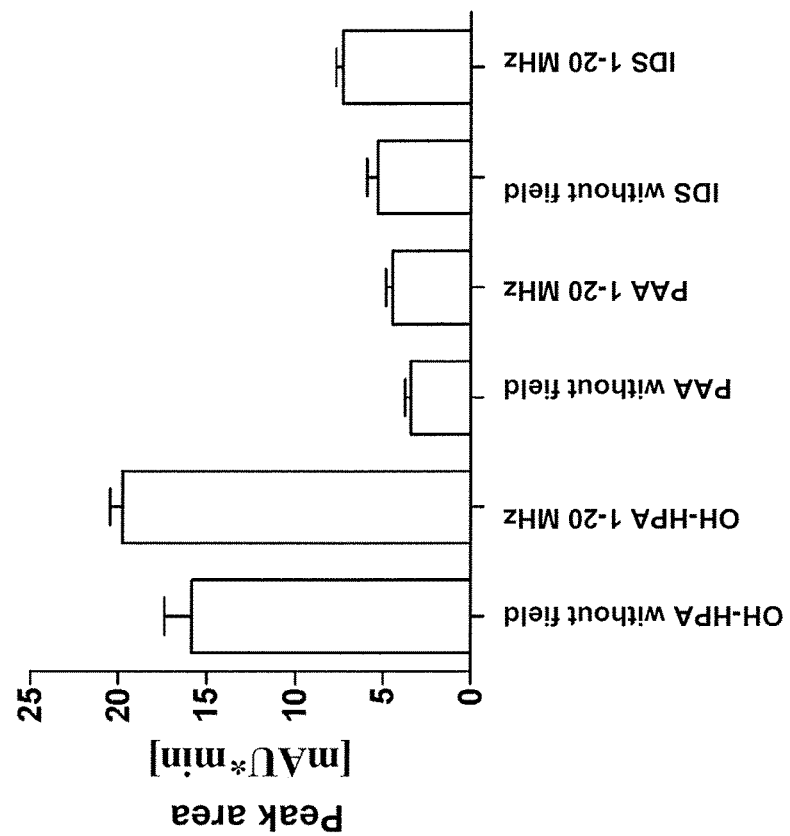
Figure 3:
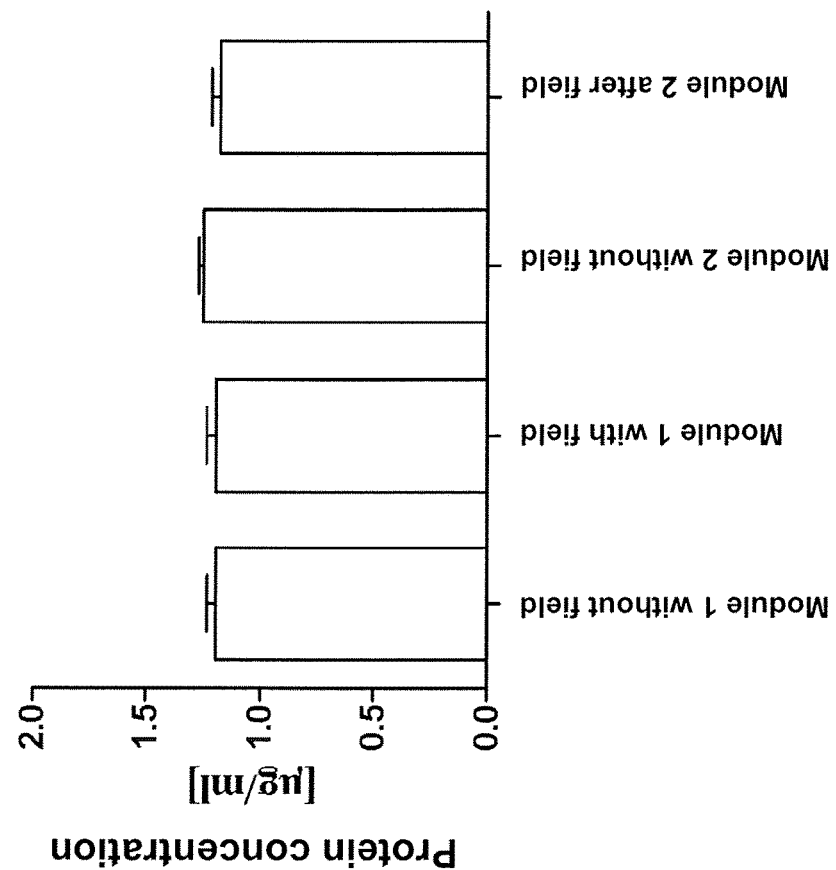
Figure 4:
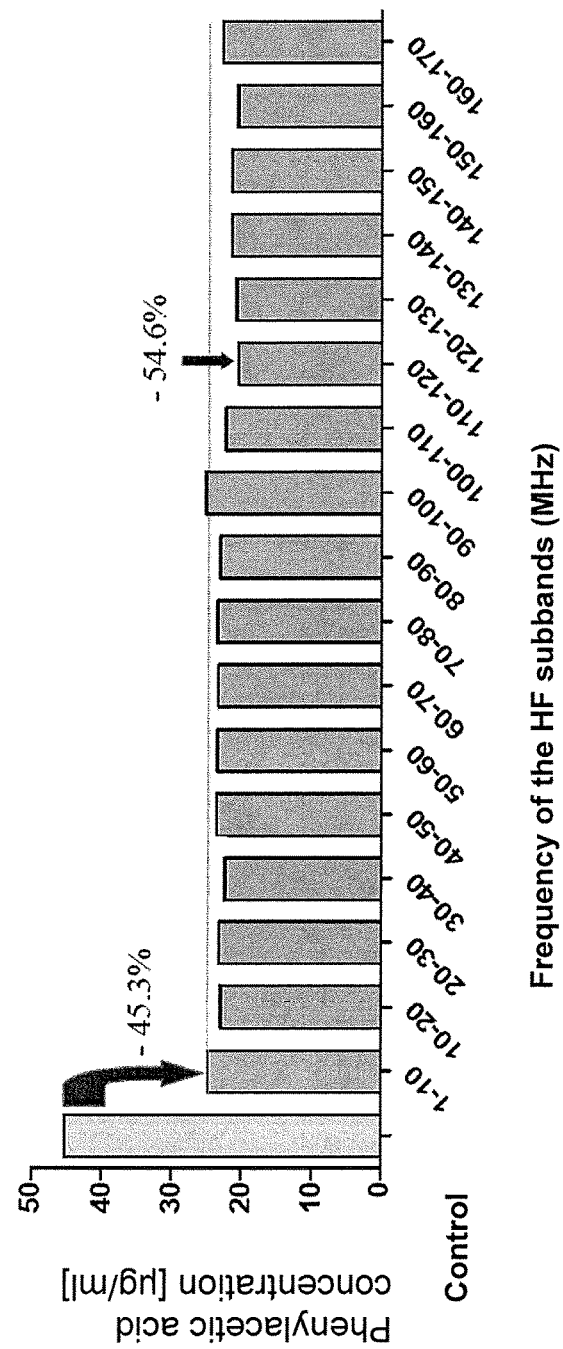
Figure 5:
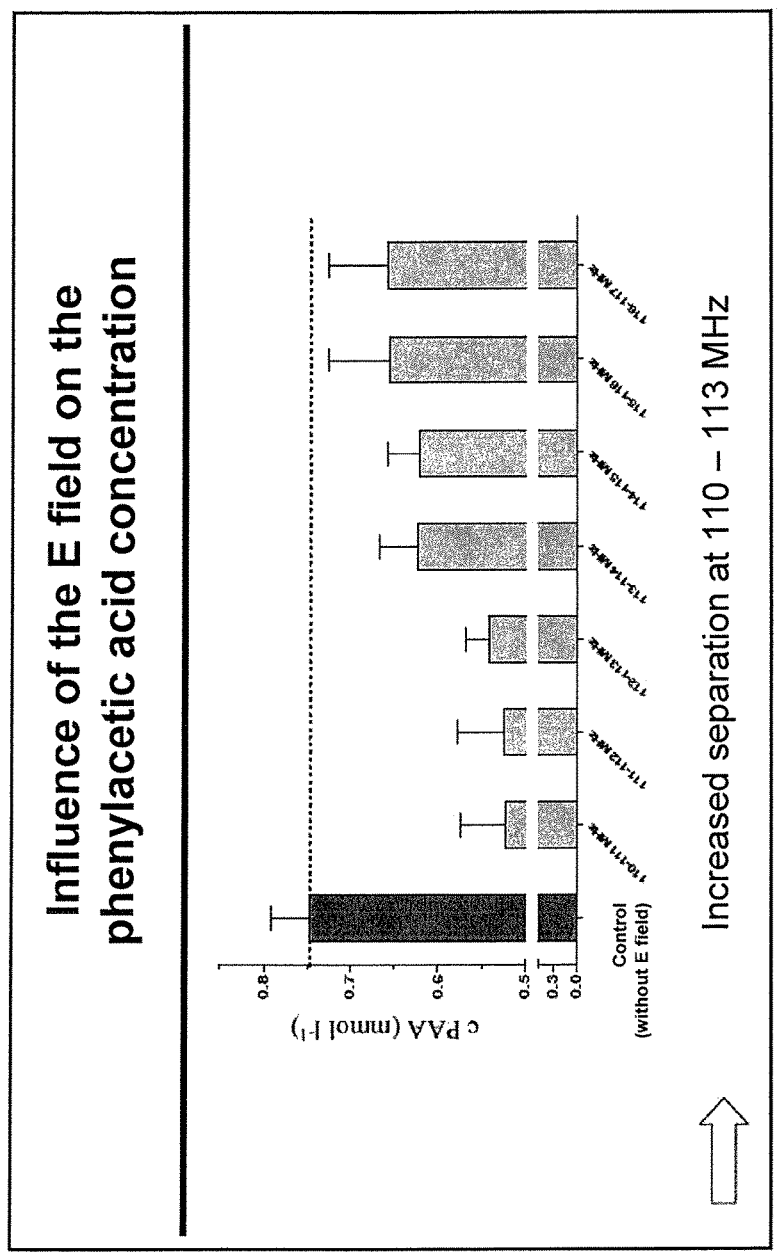
Figure 6:
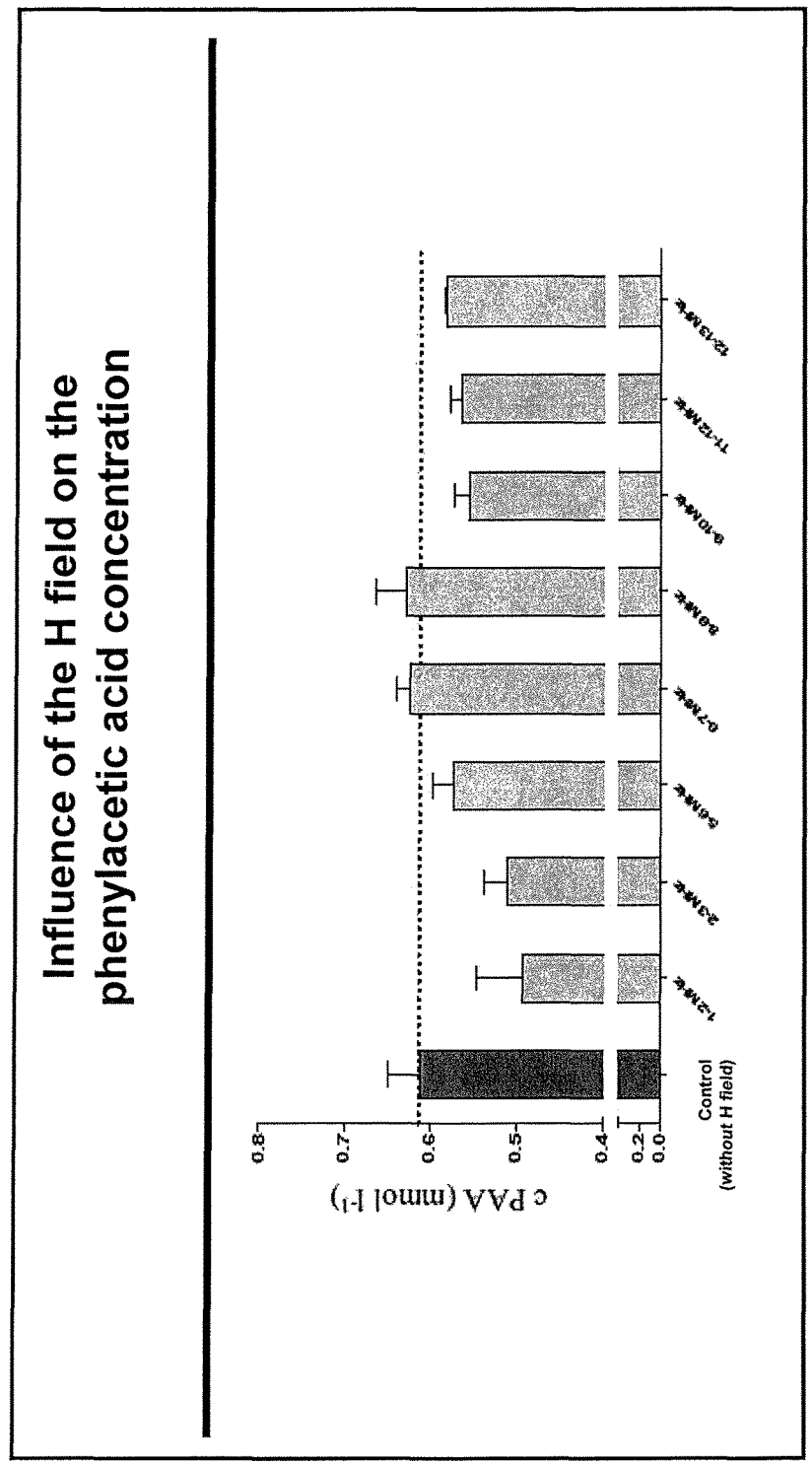
Figure 7:
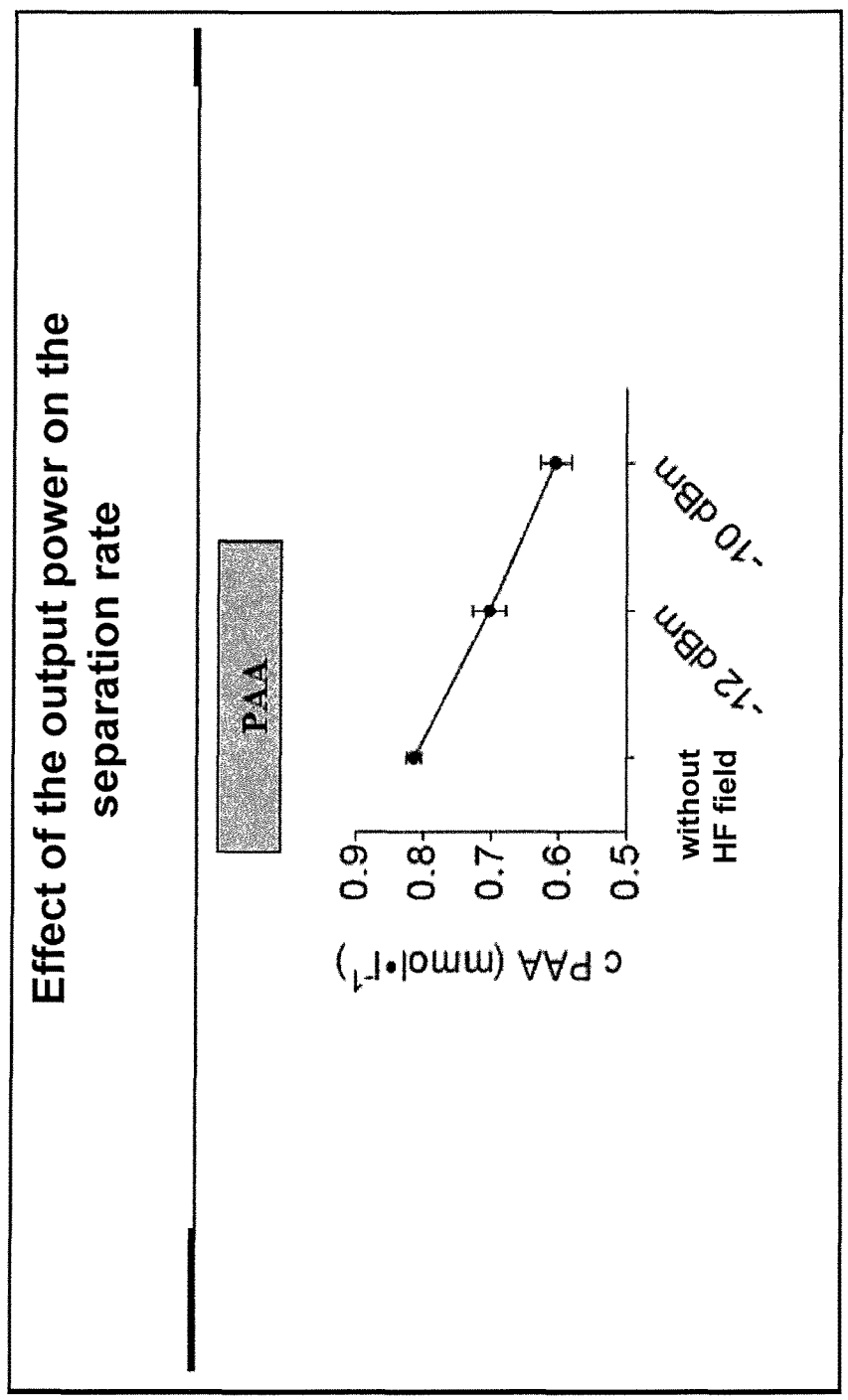

Additional details and advantages of the present invention are explained with reference to the following figures and embodiments. There are shown in the Figures:

FIG. 1 a schematic diagram of a part of the extracorporeal circulation and of the dialysis fluid circulation with a hemodialyzer and a hemofilter as well as with inlet lines for the replacement fluid;

FIG. 2: experimental results relating to the influence of high-frequency electromagnetic fields on the protein-bound portion of uremic toxins;

FIG. 3: experimental results as proof of the lack of damage to the membrane by the high-frequency fields;

FIG. 4: experimental results relating to the influences of an HF field in the frequency range 1 to 170 MHz on the protein-bound portion of uremic toxins;

FIG. 5: experimental results relating to the influences of an HF field in the frequency range 110 to 115 MHz on the protein-bound portion of uremic toxins;

FIG. 6: experimental results relating to the influences of an H field in the frequency ranges 1 to 6 MHz and 9 to 13 MHz on the protein-bound portion of the uremic toxins; and FIG. 7: experimental results relating to the influences of the field strength on the protein-bound portion of the uremic toxins.

FIG. 1 shows a part of the extracorporeal circulation 10 through which blood is circulated at the flow rate QB by means of a blood pump 11 in the direction of the arrow. A pressure sensor 40 and a sensor 50 are arranged upstream from the hemodialyzer or hemofilter 20 in the extracorporeal circulation 10 for detecting the arterial blood pressure $P_{art}$ and hematocrit $HKT_{in}$ before purification of the blood.

Appropriate measuring devices 40, 50 for detecting the corresponding values $P_{ven}$ and $HKT_{out}$ after the purification of the blood are arranged downstream from the hemodialyzer and/or hemofilter 20.

Dialysis fluid flows in countercurrent with the bloodstream in the direction of the arrow at flow rate QD through the hemodialyzer or hemofilter 20. The dialysis fluid line 30 has pressure sensors 40 upstream and downstream from the hemodialyzer or hemofilter for the respective pressure $PD_{in}$ and $PD_{out}$ of the dialysis fluid. Circulation of the dialysis fluid is controlled by pumping means and/or balancing means 31 and 32.

The hemodialyzer and/or hemofilter is/are subdivided by a semipermeable membrane 21 into a blood chamber 22 and a dialysis fluid chamber 23.

The hemodialyzer and/or hemofilter 20 is/are surrounded by means for generating a high-frequency electromagnetic field and/or an electric DC field 70.

In another embodiment, in addition to the hemodialyzer and/or hemofilter 20, a part of the extracorporeal blood circulation 10 upstream therefrom is surrounded by means for generating a high-frequency electromagnetic field and/or an electric DC field 70. Upstream and downstream from the hemodialyzer and/or hemofilter 20 there are inlet lines 12, 14 with liquid pumps 13 and/or 15 which are provided for supplying replacement fluid to the blood flowing in the extracorporeal circulation 10 during the treatment. The respective flow rates are labeled as $Q_s$pre and $Q_s$post.

The two infusion rates $Q_s$pre and $Q_s$post of the replacement fluid may be varied according to the invention with the help of the control unit 100. The control unit 100 is connected to all the actuators and sensors shown here by connections (not shown). The infusion rates are varied according to the measured values of the control values to be controlled. In the embodiment illustrated in FIG. 1, the measured values of the arterial and venous blood pressure $P_{art}$, $P_{ven}$ as well as the pressures of the dialysis fluid $P_D$in and $P_D$out before and after passing through the hemodialyzer and hemofilter 20 are shown. The resulting transmembrane pressure TMP is set or kept at the desired target level according to the present invention through a suitable modification of the flow rates $Q_s$pre and $Q_s$post at the desired target value. Instead of the transmembrane pressure TMP, hematocrit values $HKT_{in}$, $HKT_{out}$ may also be used as control values. TMP may also be approximated by using fewer than the four pressure sensors shown here. With the dialysis machines that are customary currently pressure sensors are normally used for $P_{ven}$ and $P_{Dout}$.

The effect achieved with the help of the apparatus claimed here is that the limitation membrane, which is built up on the side of the membrane of the hemodialyzer or hemofilter opposite the chamber in which the blood is present, can be kept in a stationary state, which results in a constant purification spectrum and a constant degree of purification during the treatment. At the same time, the transmembrane pressure can be kept constant during treatment because the pressure drop caused by the membrane and the limitation membrane also remains constant.

Due to the limitation of the transmembrane pressure to a predeterminable level, the risk an extensive loss of albumin through the membrane due to high convective forces can be prevented. When using high-flow membranes, the limitation of the transmembrane pressure is especially important.

Especially in patients with severe coagulation problems, the combination of pre- and postdilution contributes toward a reduction in the consumption of heparin, which is normally infused into the blood to prevent blood from coagulating in the extracorporeal circulation. When blood is diluted upstream from the hemodialyzer and/or hemofilter, less anticoagulant fluid is necessary to reduce the risk of blood coagulating in the hemodialyzer and/or hemofilter because the latter is the most significant potential for blood coagulation in the extracorporeal circulation.

Apart from the aforementioned advantages of a constant operating behavior, a good purification performance for protein-bound uremic toxins can be achieved through the combination of predilution and postdilution and through the action of a high-frequency electromagnetic field and/or an electric DC field.

The following experimental results serve as experimental proof of the effect of an electric field on the separation of protein-bound toxins during the dialysis.

The effect of an HF field in the frequency range from 1 to 20 MHz is described in embodiment 1. Embodiment 2 shows the effect of the HF field in the frequency range from 1 to 170 MHz on the separation of phenylacetic acid. The separation rate for phenylacetic acid was able to be increased by at least 45.3% under the influence of the HF field. The effect was particularly pronounced at 54.6% in the subband from 110 to 120 MHz. The subband from 110 to 120 MHz is looked at more closely in embodiment 3. Embodiment 4 shows the influence of an H field in the ranges 1-6 MHz and 9-13 MHz. Embodiment 5 shows the influence of the field strength on the separation of phenylacetic acid.

The temperature was kept constant in all embodiments 1 to 5 so that the observed changes are based on the properties of the electric field and not on a heating.

EMBODIMENT 1

The influence of high-frequency electromagnetic fields on the protein-bound portion of the uremic toxins was examined in a series of in vitro experiments.

A dialysis module was set up for this purpose in that conventional hemofiltration capillaries were cast as loops using silicone into a syringe receiving neck. An aqueous albumin solution was introduced into the respective module in the presence of the uremic toxins phenylacetic acid, p-hydroxyhippuric acid and indoxyl sulfate. This solution was filtered with the dialysis module using a syringe pump for 10 min. A high-frequency electromagnetic field was subsequently induced in the solution by using a high-frequency electrode (HF electrode). The electromagnetic field is incremented by means of a high-frequency voltage source over a period of 10 minutes from 1 to 20 MHz in steps of 1 MHz. The concentration of the uremic toxins phenylacetic acid, p-hydroxyhippuric acid and indoxyl sulfate previously added to the artificial plasma was determined in the resulting filtrates. The effect of the HF field on the bond between the proteins and the uremic toxins was able to be evaluated by a comparison of the uremic toxin concentration in the resulting filtrates.

The quantitative determination of the uremic toxin concentration in the resulting filtrates showed that high-frequency electromagnetic fields significantly increase the filtration rates of the protein-bound uremic toxins (FIG. 2).

The protein concentration in the filtrate was determined using Bradford protein dyeing to check whether high-frequency electromagnetic fields damage the dialysis membranes. The results show that no significant changes of the protein concentration can be detected in dialysis modules without and with the influence of high-frequency electromagnetic fields (FIG. 3). Macroscopic damage to the membrane can be precluded on the basis of these data.

EMBODIMENT 2

Examination of the HF field effect in the frequency range 1 to 170 MHz.

An aqueous solution of bovine serum albumin (BSA, 60 mg/ml) was introduced into the dialysis module of Example 1 in the presence of the uremic toxin phenylacetic acid (1 mmol/l in 0.9% NaCl solution). The HF field was varied in subbands of 10 MHz in the frequency range 1-170 MHz and was compared with a control experiment without an HF field.

The quantitative determination of the phenylacetic acid was performed using HPLC.

The results of the experiments are collected in FIG. 4. The separation rate for phenylacetic acid was able to be increased by at least 45.3% under the influence of the HF field. The effect was particularly pronounced at 54.6% in the subband from 110 to 120 MHz.

EMBODIMENT 3

This embodiment follows on from the examinations in accordance with Embodiment 2 which showed that the effect was particularly pronounced in the subband from 110 to 120 MHz.

In the continuing examinations in accordance with Embodiment 3, the frequency range about 110 to 115 MHz was in particular able to be identified as an effective frequency range for the release of protein-bound uremic toxins. FIG. 5 shows the respective effect on the corresponding release and the subsequent separation of phenylacetic acid.

According to the current status, the frequency ranges named summarily in Table 1 are suitable for the separation of protein-bound uremic toxins.

TABLE 1

Suitable frequencies in the HF field

| Frequencies E Field | PAA | IDS | pCRS |
|---|---|---|---|
| 80-120 MHz | 110 | 110 | 110 |
|  | 110-111 | 110-111 | 110-111 |
|  | 111 | 111 | 111 |
| 120-170 MHz | 140-141 | 140-141 | 140-141 |
|  | 148-149 |  | 151-152 |
|  | 160-161 |  |  |

The respective frequency ranges are the ranges at which the maximum separation effect was determined. An increased separation was determined in part in the non-named frequency ranges in comparison with the control; however, it was smaller than in the named frequency ranges.

EMBODIMENT 4

An increased release and thus separation of the protein-bound uremic toxins was furthermore also able to be determined in the range of the H field.

It can be seen from FIG. 6 that the H field range from 1-6 MHz and the range 9-13 MHz are suitable to release protein-bound uremic toxins from the protein bond and consequently to separate them dialytically. The effect on phenylacetic acid is shown in FIG. 6.

EMBODIMENT 5

In addition to the frequency of the field used, its field strength is also relevant to the resulting release and separation. As the field strength increases, the respective uremic toxins are increasingly released from the protein bond and are subsequently separated.

FIG. 7 shows the effect of an increasing field strength on the content of protein-bound uremic toxins in the retentate for the example of phenylacetic acid.

The invention claimed is:

1. A hemodiafiltration device comprising:
a hemodialyzer/hemofilter separated by a membrane into a blood circulation chamber and dialysis fluid circulation chamber;
an extracorporeal blood circulation line extending upstream and downstream of the blood circulation chamber and having at least one replacement-fluid inlet line upstream and at least one replacement-fluid inlet line downstream of said blood circulation chamber;
at least one measurement apparatus for recording at least one of transmembrane pressure, difference between upstream and downstream hematocrit (HKT), and difference between upstream and downstream blood density;
a control unit connected to the at least one measurement apparatus and constructed for control of at least one of the transmembrane pressure, the hematocrit, and the blood density by controlling the upstream and downstream infusion rates of the replacement fluid ($Q_s$pre, $Q_s$post) based on input received from the at least one measurement apparatus; and
a high-frequency electromagnetic field generator configured to generate a field having a frequency of 1 MHz to 1 GHz arranged to surround the hemodialyzer/hemofilter or a part of the extracorporeal blood circulation line extending upstream of the hemodialyzer/hemofilter and the hemodialyzer/hemofilter in order to expose blood during or before an during passing through the blood circulation chamber to a high-frequency electromagnetic field.

2. The device according to claim 1 further comprising
f) a dialysis fluid circulation line extending upstream and downstream of the dialysis fluid circulation chamber, and
g) pressure sensors arranged in the dialysis fluid circulation line upstream and downstream of the dialysis fluid circulation chamber, respectively.

3. The device according to claim 1, wherein the control unit is configured to control the infusion rates ($Q_s$pre, $Q_s$post) of the replacement fluid so that $Q_s$pre is greater than or equal to $Q_s$post during hemodiafiltration treatment.

4. The device according to claim 1, wherein the control unit is configured to control the infusion rates ($Q_s$pre, $Q_s$post) of the replacement fluid so that the ratio of the infusion rates $Q_s$pre/$Q_s$post is at least 1.2.

5. The device according to claim 1, wherein the control unit is configured to control the infusion rates ($Q_s$pre, $Q_s$post) of the replacement fluid so that the ratio of the infusion rates $Q_s$pre/$Q_s$post is at least 1.5.

6. The device according to claim 1, wherein the high-frequency electromagnetic field generator is a high-frequency coil, a high-frequency electrode, or a high-frequency capacitor.

7. The device according to claim 1, wherein the high-frequency electromagnetic field generator has an output power greater than −12 Db.

8. The device according to claim 1, wherein the high-frequency electromagnetic field generator is configured to generate a field having a frequency of 10 MHz-1 GHz.

9. The device according to claim 1, wherein the high-frequency electromagnetic field generator is configured to generate a field having a frequency of 20 MHz-1 GHz.

* * * * *